Figure 1:
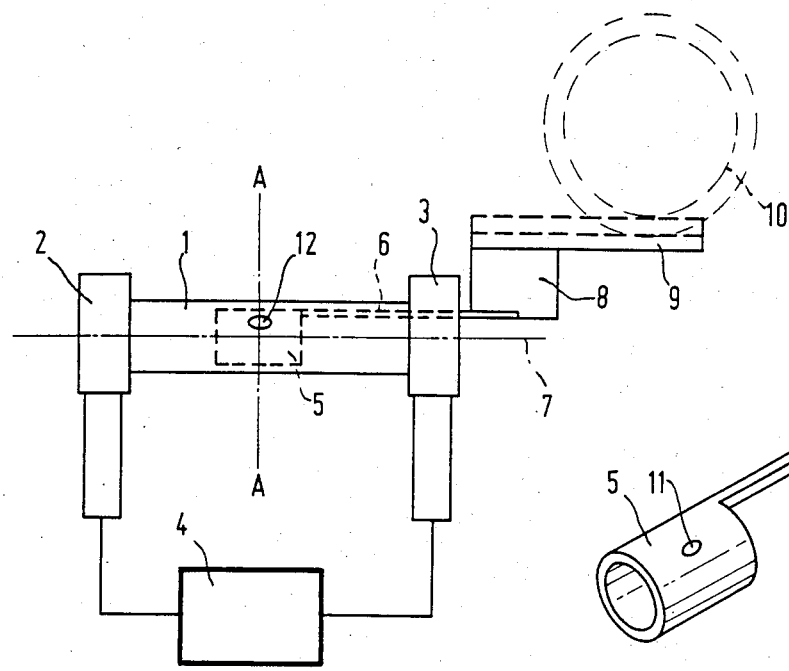

United States Patent [19]

Littlejohn

[11] Patent Number: 4,657,389
[45] Date of Patent: Apr. 14, 1987

[54] ELECTROTHERMAL ATOMIZER

[75] Inventor: David Littlejohn, East Kilbride, Scotland

[73] Assignee: U.S. Philips Corporation, New York, N.Y.

[21] Appl. No.: 749,051

[22] Filed: Jun. 26, 1985

[30] Foreign Application Priority Data

Jul. 9, 1984 [GB] United Kingdom ............... 8417440

[51] Int. Cl.⁴ ............................................. G01N 21/74
[52] U.S. Cl. .................................... 356/312; 356/244
[58] Field of Search ....................... 356/312, 244, 312

[56] References Cited

U.S. PATENT DOCUMENTS

| 3,824,016 | 7/1974 | Woodriff et al. | 356/312 |
| 3,895,873 | 7/1975 | Dennison et al. | 356/312 |
| 4,111,563 | 9/1978 | Tamm | 356/312 |
| 4,407,582 | 10/1983 | Woodriff | 356/312 |
| 4,443,105 | 4/1984 | Huber et al. | 356/312 |
| 4,534,646 | 8/1985 | Tamm et al. | 356/312 |

FOREIGN PATENT DOCUMENTS 2071314  9/1981  United Kingdom .

Primary Examiner—F. L. Evans
Attorney, Agent, or Firm—Paul R. Miller

[57] ABSTRACT

An electrothermal atomizer comprises a cuvette (1) clamped between two electrodes (2,3) to which an electrical power supply (4) is connected. A probe comprising a tubular head portion (5) and a stem portion (6) is insertable in and removable from the cuvette (1) by means of a rack (9) driven by a motor via a gear (10).

By making the probe head (5) in the form of a tube, a large sample volume can be accommodated, and by forming the stem (6) at the top of the tube (5), spreading of acid samples along the stem during the drying phase is minimized.

8 Claims, 5 Drawing Figures

ELECTROTHERMAL ATOMIZER

The invention relates to an electrothermal atomiser for a spectrophotometer with the atomiser comprising a hollow body of electrically conductive material, means for depositing a sample on a probe, means for inserting the probe into the interior of the hollow body, and means for passing an electrical current through the hollow body to heat the interior of the hollow body to a temperature which is sufficient to atomise the sample.

Such an atomiser is disclosed in U.K. Patent Application No. 2136144A. In this atomiser the probe was formed of pyrolytic graphite as was the preferred form of hollow body (or cuvette). An atomiser as set forth in the opening paragraph has also been disclosed in U.K. Patent Application No. 2088582A in which the probe (or sample carrier) is formed of graphite of unspecified type. U.K. Patent Application No. 2071845 discloses such an atomiser in which the probe is in the form of a wire (tungsten) filament. U.K. Patent Application No. 2113128A discloses a probe made from glassy carbon.

It has been found that probes made from pyrolytic graphite and glassy carbon and probes coated with pyrolytic graphite suffer from the disadvantage of sample spreading when samples contain more than about 0.5% v/v of nitric acid. The reduced surface tension of such solutions causes the sample to spread irreproducibly up the probe stem during the drying phase. Various proposals have been made in an attempt to overcome this problem. The initial experiments were conducted with the probe inserted into the cuvette through a slot in the wall in a manner as described in U.K. Patent Application No. 2136144A. With this configuration only the probe head is heated significantly during the drying phase, while the stem, outside the cuvette, remains cool. It was thought that the sharp temperature gradient along the probe could be responsible for the spreading phenomenon, as the liquid sample would tend to travel to the cooler region outside the cuvette.

The alternative configuration, or the 'end entry' probe, allows the probe to enter the cuvette parallel to its longitudinal axis. It is therefore no longer necessary to cut a slot in the cuvette, and accordingly improved cuvette lifetimes and sensitivity would be expected. The temperature gradient along the probe would now also be much less steep, as a large part of the stem as well as the head would be heated. It was throught that the spreading problem would therefore be alleviated, and that even if some spreading did occur, as much more of the probe stem would be introduced into the hot zone during the atomisation phase, the effects might be less significant.

Such an arrangement was tried and initial results using glassy carbon probes with a pyrolytic graphite coating were promising. However on repeating the measurement it was found that the performance deteriorated until there was no significant improvement in controlling sample spreading over the front entry system.

Other approaches were to use microporous glassy carbon probes with either the head or the stem pyrolytically coated. It was found that coating the head and leaving the stem uncoated gave no significant advantage over a fully coated probe while coating the stem and leaving the head uncoated gave a worse performance.

A further approach was to deposit the sample onto a hot probe. However, with the arrangement used in which the probe is heated by the cuvette it was not found to be practicable as the sample boiled inside the pipette before it could be deposited on the probe. It is considered, however, that this arrangement could be advantageous if the probe is heated independently of the cuvette.

All these attempts at solving the problem of sample spreading have proved unsuccessful and appear to make the use of probe atomisation unsatisfactory for all but a minority of practical samples.

It is an object of the invention to enable the provision of an electrothermal atomiser in which the sample is atomised off a probe inserted into a hollow body which is capable of handling acid samples.

The invention provides an electrothermal atomiser as set forth in the opening paragraph characterised in that the probe comprises a cylindrical head portion and a stem portion, the stem portion being attached to the head portion in such a position that it is spaced from the sample deposition zone so that the sample is prevented from spreading along the stem portion.

The separation of the stem portion from the sample deposition zone reduces the problem of sample spreading by breaking the path between the stem portion and the sample deposition zone. This separation can be achieved without the use of a step and hence the problem of a double peak being produced by the slower heating of the step portion can be overcome.

An electrothermal atomiser in which the hollow body is tubular, open at both ends and is mounted with its longitudinal axis horizontal with means being provided to insert the probe into the hollow body in a direction parallel to its longitudinal axis may be characterised in that the probe stem is connected to the head portion at a position above the longitudinal axis of the head portion.

This provides an effective separation between the sample deposition zone and the stem portion in a particularly simple manner and allows a construction in which a relatively large sample volume can be deposited. Further by inserting the probe along the longitudinal axis the need for a slot in the side wall for probe entry is eliminated enabling a standard cuvette to be used. This has the advantage of lower cost and a longer lifetime, particularly if electrographite cuvettes are used, as slotted cuvettes tend to be eroded in the area of the slot.

An electrothermal atomiser in which the hollow body is tubular, open at both ends, has a longitudinal slot in its wall and is mounted with its longitudinal axis horizontal, means being provided to insert the probe into the hollow body through the slot in a direction transverse to the longitudinal axis may be characterised in that the stem portion is connected to the head portion at a region remote from the ends of the head portion.

By inserting the probe in a direction transverse to the longitudinal axis a convenient mechanical construction can be achieved with the insertion means well away from the optical path but since the tubular head portion of the probe will cross the optical path on insertion, determination of the background radiation may be rendered more difficult.

The head portion of the probe may be provided with a sample dosing aperture. This provides a simple and convenient means for introducing a sample into the head portion. The sample dosing aperture in the head portion is aligned with a sample dosing aperture in the hollow body when the head portion is located within the hollow body.

This enables the method of atomising a sample disclosed in U.K. Patent Application No. 2136144A to be performed using this embodiment of electrothermal atomiser, i.e. the sample can be deposited within the probe head through the two aligned apertures.

Figure 2:
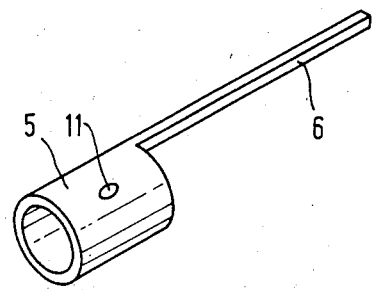
Figure 3:
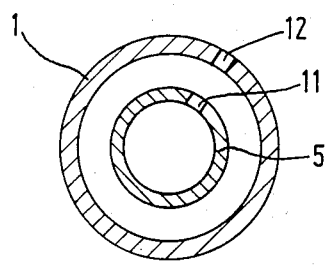
Figure 5:
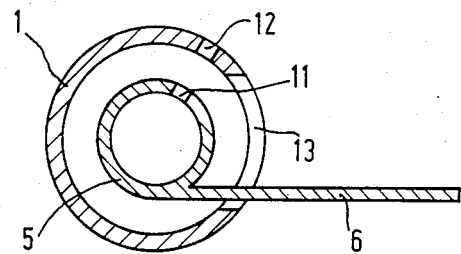
Figure 4:
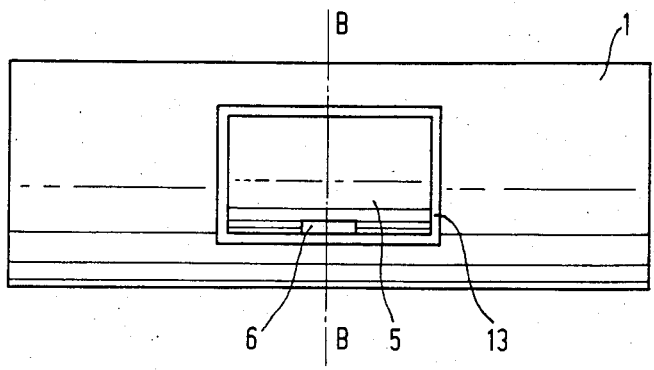

Embodiments of the invention will now be described, by way of example, with reference to the accompanying drawings, in which:

FIG. 1 shows in schematic form an electrothermal atomiser according to the invention, FIG. 2 is a perspective view of a probe for use in the atomiser of FIG. 1, FIG. 3 is a cross-sectional view on line A—A of the hollow body and probe of FIG. 1, FIG. 4 is a side elevation of a hollow body and probe for use in an alternative electrothermal atomiser according to the invention, and FIG. 5 is a cross-sectional view on line B—B of FIG. 4.

FIG. 1 shows in schematic form an electrothermal atomiser which comprises a hollow body 1 of electrically conductive material in the form of a tubular graphite body. The hollow body 1 may be formed, for example, of pyrolytic graphite but may be of other suitable materials such as electrographite, glassy carbon or refractory metals. The hollow body 1 (hereinafter referred to as a cuvette) is clamped between two electrodes 2 and 3 to which an electric power supply 4 is connected. A probe which comprises a tubular head portion 5 and a stem portion 6 is arranged to be inserted into the cuvette 1 along its longitudinal axis 7. The probe stem 6 is carried by a member 8 which is mounted on a rack 9 which engages with a gear 10 driven by a motor (not shown). Thus the probe may be inserted into and withdrawn from the cuvette 1 in the direction of the longitudinal axis 7 by operation of the motor. Clearly many other means for insertion and withdrawal of the probe could be substituted for the means shown with such alternative means being readily apparent to a mechanical designer.

The probe shown in FIGS. 1 and 2 comprises a tubular head portion 5 of circular cross-section from the highest point of which, in operation, extends the stem portion 6. Thus a large sample may be deposited in the head portion 5 with minimal risk of the sample spreading along the stem portion 6. This is in contrast with the normal flat or cupped probe in which the head portion and stem portion meet in the same plane as the sample deposition zone, and hence, there is at most only a small barrier to prevent the sample spreading up the stem. The probe shown in FIGS. 1 and 2 may be produced taking a cylindrical body and forming the stem portion by cutting away all except a thin strip for the length of the stem portion. The head portion may be provided with a dosing aperture 11 through which a sample may be deposited into its interior. The probe may be formed from graphite and conveniently may be formed totally of pyrolytic graphite but may also be constructed from other suitable materials such as electrographite or glassy carbons.

The cuvette 1 may be provided with a dosing aperture 12 which when the probe is inserted in the cuvette is aligned with the aperture 11 in the probe. This enables the method of atomising a sample disclosed in U.K. Patent Appliction No. 2136144A to be performed using the atomiser shown in FIG. 1. Thus to perform this method the probe is inserted in the cuvette 1 so that the apertures 11 and 12 are aligned, a sample is deposited through the aligned apertures, either manually or by using an autosampler, and the cuvette 1 is then heated by the passage of electrical current from the power supply 4 to a temperature sufficient to dry the sample and, depending on the nature of the sample, to ash it. The probe is then withdrawn from the cuvette 1 until its temperature has stablised at the atomising temperature when the probe is re-inserted to atomise the sample.

FIGS. 4 and 5 show a probe and cuvette modified for entry of the probe in a direction transverse to the longitudinal axis of the cuvette 1. The cuvette 1 is provided with a longitudinally extending slot 13 through which the probe head 5 is inserted. The stem portion 6 of the probe extends from the outside cylindrical surface of the head portion 5 and does not extend as far as the ends of the tubular head portion 5 thus minimising the possibility of the sample spreading along the stem portion 6. The cuvette 1 may additionally be provided with a dosing aperture 12 but alternatively this could be combined with the slot 13. Although the slot 13 is necessarily larger than the equivalent slot in a cuvette for use with a flat probe the problem of sample loss through the slot is not likely to be severe as the sample will be largely confined within the probe head portion 6. A disadvantage of this configuration is that when the probe is inserted into the cuvette 1, it will cut the optical path and thus produce a disturbing signal on the instrument baseline on insertion. However it has the advantage of fewer constraints on the mechanical positioning means since these are well away from the optical path.

A probe as shown in FIG. 2 has been prepared from a 5 mm diameter cylindrical pyrolytic graphite cuvette by cutting away the tube portion not required so that a head portion about 6 mm long was formed with the rest of the length of the cuvette being cut away to form the stem. The probe was inserted into a cuvette having a diameter of 7.5 mm. It was found that it is possible to inject samples of more than 40 μL onto the probe and that satisfactory drying of samples containing up to 8% v/v $HNO_3$ was possible. Optical pyrometer measurements of the probe head temperature indicated that the cylindrical head portion attained a temperature 2°–300° C. lower than the cuvette temperature.

I claim:

1. An electrothermal atomizer for a spectrophotometer comprising a hollow electrically conductive body, probe means for inserting a sample into said hollow body, and means for electrically heating said hollow body to a temperature for atomizing said sample, the improvement comprising said probe means including a hollow tubular head portion for holding said sample and a stem portion attached to said head portion at a position removed from said sample to prevent sample spreading along said stem portion.

2. An electrothermal atomizer according to claim 1, wherein said hollow body is a tubular member open at opposite ends, said tubular member being mounted with a horizontal longitudinal axis, wherein means are provided for inserting said probe means into said hollow body in a direction parallel to said longitudinal axis, and wherein said stem portion is connected to said head portion at a position above the longitudinal axis of said head portion.

3. An electrothermal atomizer according to claim 1, wherein said hollow body is a tubular member open at opposite ends, said tubular member being mounted with a horizontal longitudinal axis, wherein means are provided for inserting said probe means into said hollow body through a slot in a direction transverse to said longitudinal axis, and wherein said stem portion is connected to said head portion at a region remote from ends of said head portion.

4. An electrothermal atomizer according to claim 1 or claim 2 or claim 3, wherein said head portion has a sample dosing aperture.

5. An electrothermal atomizer according to claim 4, wherein said hollow body has a sample dosing aperture, and said sample dosing aperture of said hollow body and said sample dosing aperture of said head portion are aligned when said head portion is provided in said hollow body.

6. An electrothermal atomizer according to claim 1 or claim 2, wherein said stem portion is a thin elongated member attached to said head portion.

7. An electrothermal atomizer according to claim 6 wherein said head portion is a tubular member having a circular cross-section of a size to fit within said hollow body.

8. An electrothermal atomizer according to claim 3, wherein said head portion is a tubular member having a circular cross-section of a size to fit within said hollow body.

* * * * *